United States Patent [19]
Kumar

[11] Patent Number: 5,808,063
[45] Date of Patent: Sep. 15, 1998

[54] PHOTOCHROMIC SPIRO(INDOLINE) FLUORANTHENOXAZINE COMPOUNDS

[75] Inventor: Anil Kumar, Pittsburgh, Pa.

[73] Assignee: PPG Industries, Inc., Pittsburgh, Pa.

[21] Appl. No.: 942,181

[22] Filed: Oct. 1, 1997

[51] Int. Cl.$^6$ .................................. C07D 498/10
[52] U.S. Cl. ................ 544/71; 351/162; 351/163; 359/674; 523/106; 524/90; 524/97; 252/586
[58] Field of Search ............... 544/70, 71; 351/162, 351/163; 359/674; 524/90, 97; 523/106; 252/586

[56] References Cited

U.S. PATENT DOCUMENTS

| | | | |
|---|---|---|---|
| 3,361,706 | 1/1968 | Meriwether et al. | 260/39 |
| 3,562,172 | 2/1971 | Ono et al. | 252/300 |
| 3,567,605 | 3/1971 | Becker et al. | 260/39 |
| 3,578,602 | 5/1971 | Ono et al. | 252/300 |
| 4,215,010 | 7/1980 | Hovey et al. | 252/300 |
| 4,342,668 | 8/1982 | Hovey et al. | 252/586 |
| 4,360,653 | 11/1982 | Stevens et al. | 526/301 |
| 4,816,584 | 3/1989 | Kwak et al. | 544/71 |
| 4,818,096 | 4/1989 | Heller et al. | 351/163 |
| 4,826,977 | 5/1989 | Heller et al. | 544/70 |
| 4,880,667 | 11/1989 | Welch | 427/160 |
| 4,931,219 | 6/1990 | Kwiatkowski et al. | 252/586 |
| 4,931,220 | 6/1990 | Haynes et al. | 252/586 |
| 4,994,208 | 2/1991 | McBain et al. | 252/586 |
| 5,000,878 | 3/1991 | Chu | 252/587 |
| 5,066,818 | 11/1991 | Van Gemert et al. | 549/289 |
| 5,200,483 | 4/1993 | Selvig | 526/301 |
| 5,238,981 | 8/1993 | Knowles | 524/110 |
| 5,274,132 | 12/1993 | Van Gemert | 549/389 |
| 5,373,033 | 12/1994 | Toh et al. | 822/96 |
| 5,384,077 | 1/1995 | Knowles | 252/586 |
| 5,405,958 | 4/1995 | Van Gemert | 544/71 |
| 5,429,774 | 7/1995 | Kumar | 252/586 |
| 5,458,814 | 10/1995 | Kumar et al. | 252/586 |
| 5,466,398 | 11/1995 | Van Gemert et al. | 252/586 |
| 5,475,074 | 12/1995 | Matuoka et al. | 526/336 |
| 5,514,817 | 5/1996 | Knowles | 549/384 |
| 5,552,090 | 9/1996 | Van Gemert et al. | 252/586 |
| 5,552,091 | 9/1996 | Kumar | 252/586 |
| 5,565,147 | 10/1996 | Knowles et al. | 252/586 |
| 5,573,712 | 11/1996 | Kumar et al. | 252/586 |
| 5,578,252 | 11/1996 | Van Gemert et al. | 252/586 |
| 5,645,767 | 7/1997 | Van Gemert | 252/586 |

OTHER PUBLICATIONS

Campbell et al., "Syntheses of Fluoranthene and its Derivatives from 7:8–Dialkylacenaphthene–7:8 diols", J. Chem. Soc., 1949, pp. 1555–1559.

Campbell et al., "The Interaction of 2–Benzylideneacenaphthene–1–one and Ethyl Acetoacetate", J. Chem. Soc., 1963, pp. 1511–1513.

Campbell et al., "Bromination of 3–Methoxyfluroanthene", J. Chem. Soc., 1969, pp. 1697–1969.

Campbell et al., "The synthesis of derivatives of fluorene and fluoranthene", Chem. Abs., vol. 55, No. 24703i, 1961.

Sieglitz et al., "3–Hydroxyfluoranthene–1–, –2–, and –10–carboxylic acids", Chem. Abs., vol. 58, No. 7882b, 1963.

Sieglitz et al., "3–Hydroxyfluoranthenes", Chem. Abs., vol. 59, No. 15230h, 1963.

Shenbor et al., "Synthesis and Properties of 12–Derivatives of Fluoranthene", J. Org. Chem. of the USSR, vol. 4, No. 12, 1968, pp. 2124–2203.

Robinson, *The Fisher Indole Synthesis,* John Wiley & Sons Ltd., Table of Contents submitted herewith, 1982.

*Primary Examiner*—Richard L. Raymond
*Attorney, Agent, or Firm*—Irwin M. Stein; Frank P. Mallak

[57] ABSTRACT

Described are novel photochromic spiro(indoline) fluoranthenoxazine compounds having certain substituents on the 1 and 3 positions of the indoline portion of the compounds and which may be represented by the following graphic formula:

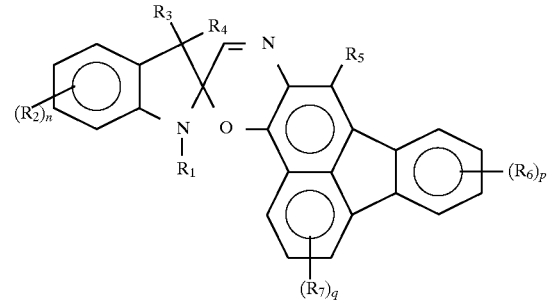

Also described are polymeric organic host materials that contain or that are coated with such compounds.

23 Claims, No Drawings

PHOTOCHROMIC SPIRO(INDOLINE) FLUORANTHENOXAZINE COMPOUNDS

The present invention relates to certain novel spiro(indoline)fluoranthenoxazine compounds. More particularly, this invention relates to novel photochromic spiro(indoline)fluoranthenoxazine compounds, and to compositions and articles containing such novel fluoranthenoxazine compounds. When subjected to ultraviolet irradiation, photochromic compounds become activated and change light transmission properties. When the ultraviolet light source is removed, these activated photochromic compounds revert to their original color or inactivated state.

The photochromism of certain spiro(indoline)naphthoxazine compounds is well known and is disclosed, for example, in U.S. Pat. Nos. 3,562,172, 3,578,602, and 4,342,668. The compounds described in U.S. Pat. Nos. 3,562,172 and 3,578,602 are naphthoxazine derivatives with substituents in the indoline portion of the molecule. U.S. Pat. No. 4,342,668 describes naphthoxazine derivatives with substituents on the 8' or 9' position, one of which substituents is halogen or lower alkoxy, the other being hydrogen. These compounds have been described as having enhanced photocolorability, i.e., a relatively large change in optical density between the activated and inactivated state.

U.S. Pat. No. 5,405,958 discloses photochromic spiro(indoline)naphthoxazine compounds with certain substituents on the 8' and 9' positions of the naphthoxazine portion of the molecule. These compounds are reported to have improved photocolorability and unexpectedly higher absorption maxima than the corresponding unsubstituted compounds.

The present invention relates to novel spiro(indoline)fluoranthenoxazines which have certain substituents at the 1 and 3 positions of the indoline portion of the compound. Photochromic compounds of the present invention include compounds that exhibit acceptable photochromic performance properties, such as activated intensity, coloration rate and fade rate.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantages they offer, vis-a-vis, glass lenses. Moreover, photochromic transparencies for vehicles such as cars and airplanes have been of interest because of the potential safety features that such transparencies offer.

In accordance with the present invention, it has now been discovered that certain novel spiro(indoline) fluoranthenoxazine compounds may be prepared. These compounds may be described as spiro(indoline)fluoranthenoxazines having certain substituents at the 1 and 3 positions of the indoline portion. Certain other substituents may be present at the 4, 5, 6 or 7 positions of the indoline portion. Other specific substituents may also be present at the 1', 2', 3', 8', 9', 10', 11' or 12' ring atoms of the fluoranthene portion.

The foregoing described spiro(indoline)fluoranthenoxazine compounds may be represented by the following graphic formula I in which numbers 1' through 12' identify the ring atoms of the fluoroanthenoxazine portion and numbers 1 through 7 identify the ring atoms of the indoline portion:

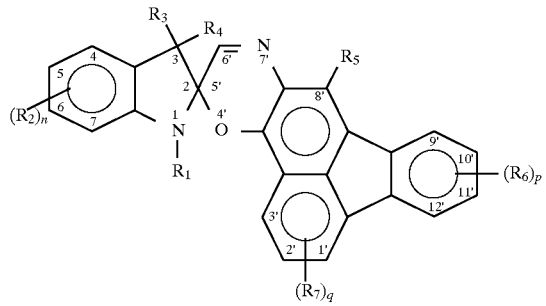

In graphic formula I, $R_1$ may be a $C_1$–$C_8$ alkyl, phen($C_1$–$C_4$)alkyl, naphth($C_1$–$C_4$)alkyl, allyl, acrylyloxy($C_2$–$C_6$) alkyl, methacrylyloxy($C_2$–$C_6$)alkyl, $C_2$–$C_4$ acyloxy($C_2$–$C_6$) alkyl, carboxy($C_2$–$C_6$)alkyl, cyano($C_2$–$C_6$)alkyl, hydroxy($C_2$–$C_6$)alkyl, $C_1$–$C_6$ alkoxy($C_2$–$C_4$)alkyl or $(C_2H_4O)_m$·$CH_3$, wherein m is an integer from 1 to 6. Preferably, $R_1$ is allyl, $C_1$–$C_3$ alkoxy($C_2$–$C_4$)alkyl or $C_1$–$C_4$ alkyl, e.g., methyl, ethyl, propyl or butyl.

Each $R_2$ may be a $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl or $C_1$–$C_4$ polyhaloalkyl, such as 1-fluoro-3-chloropropyl. Preferably, $R_2$ is $C_1$–$C_3$ alkoxy, e.g., methoxy, ethoxy or propoxy, or $C_1$–$C_3$ alkyl, e.g., methyl, ethyl or propyl. The halogen and halo substituents may be chloro, fluoro, iodo or bromo, preferably chloro or fluoro, and n is the integer 0, 1 or 2, preferably the integer 0 or 1.

$R_3$ and $R_4$ may each be $C_1$–$C_5$ alkyl, benzyl, phenyl, mono- or di-substituted phenyl, said phenyl substituents being $C_1$–$C_5$ alkyl or $C_1$–$C_5$ alkoxy, or $R_3$ and $R_4$ may together form a saturated cyclic ring containing from 5 to 8 carbon atoms which includes the spiro carbon atom, norbornyl or adamantyl. Preferably, each $R_3$ and $R_4$ is a $C_1$–$C_3$ alkyl, i.e., methyl, ethyl or propyl, or $R_3$ and $R_4$ may together form a cyclic ring containing from 5 to 7 carbon atoms which includes the spiro carbon atom.

$R_5$ in graphic formula I may be hydrogen, the group, —$CH_2X$ or —$C(O)W$, wherein X is halogen, hydroxy, benzoyloxy, $C_1$–$C_6$ alkoxy, $C_2$–$C_6$ acyloxy, amino, $C_1$–$C_6$ mono-alkylamino, $C_1$–$C_6$ dialkylamino, i.e., di($C_1$–$C_6$) alkylamino, morpholino, piperidino, 1-indolinyl, pyrrolidyl, trimethylsilyloxy, or the group, —$OCH(R_8)Z$; W may be the group, —$OCH(R_8)Z$ or an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl; Z may be —CN, —$CF_3$, halogen, —$C(O)R_8$, or —$COOR_8$; $R_8$ may be hydrogen or $C_1$–$C_6$ alkyl; the heterocyclic ring substituents may be $C_1$–$C_6$ alkyl or $C_1$–$C_6$ alkoxy; or W may be —$OR_9$ or —$N(R_{10})R_{11}$, wherein $R_9$ is hydrogen, allyl, $C_1$–$C_6$ alkyl, e.g., methyl, ethyl, propyl, butyl, pentyl, and hexyl, phenyl, mono($C_1$–$C_6$)alkyl substituted phenyl, mono($C_1$–$C_6$) alkoxy-substituted phenyl, phenyl($C_1$–$C_3$)alkyl, mono($C_1$–$C_6$)alkyl substituted phenyl($C_1$–$C_3$)alkyl, mono($C_1$–$C_6$)alkoxy substituted phenyl($C_1$–$C_3$)alkyl, $C_1$–$C_6$ alkoxy($C_2$–$C_4$)alkyl, or $C_1$–$C_6$ haloalkyl; and $R_{10}$ and $R_{11}$ may each be selected from the group consisting of hydrogen, $C_1$–$C_6$ alkyl, $C_5$–$C_7$ cycloalkyl, phenyl and mono- or di-substituted phenyl; each of the phenyl substituents being $C_1$–$C_6$ alkyl or $C_1$–$C_6$ alkoxy; and each of the halogen or halo groups being fluoro or chloro.

Preferably, $R_5$ is hydrogen, the group, —$CH_2X$ or —$C(O)$ W, wherein X is hydroxy, $C_1$–$C_4$ alkoxy, or $C_2$–$C_4$ acyloxy, W is the group, —$OCH(R_8)Z$, or an unsubstituted or monosubstituted heterocyclic ring selected from the group consisting of 1-indolinyl, morpholino, piperidino, and 1-pyrrolidyl, wherein Z is —CN, —C(O)R$_8$, or —COOR$_8$, R$_8$ is hydrogen or C$_1$–C$_4$ alkyl; and the heterocyclic ring substituents are C$_1$–C$_4$ alkyl or C$_1$–C$_4$ alkoxy; or W may be the groups —OR$_9$ or —N(R$_{10}$)R$_{11}$, wherein R$_9$ is hydrogen, C$_1$–C$_4$ alkyl, phenyl, mono(C$_1$–C$_4$)alkyl substituted phenyl, mono(C$_1$–C$_4$)alkoxy substituted phenyl, phenyl(C$_1$–C$_2$) alkyl, mono(C$_1$–C$_4$)alkyl substituted phenyl(C$_1$–C$_2$)alkyl, mono(C$_1$–C$_4$)alkoxy substituted phenyl(C$_1$–C$_2$)alkyl, mono (C$_1$–C$_4$)alkoxy(C$_2$–C$_3$)alkyl, or C$_1$–C$_4$ haloalkyl; and R$_{10}$ and R$_{11}$ may each be selected from the group consisting of hydrogen, C$_1$–C$_4$ alkyl, C$_5$–C$_7$ cycloalkyl, phenyl and mono- or di-substituted phenyl, each of the phenyl substituents being C$_1$–C$_4$ alkyl or C$_1$–C$_4$ alkoxy and each of the halo groups being fluoro or chloro.

More preferably, R$_5$ is selected from the group consisting of hydrogen, —CH$_2$X, and —C(O)W, wherein X is hydroxy, C$_1$–C$_4$ alkoxy, or C$_2$–C$_4$ acyloxy and W is an unsubstituted or mono-substituted heterocyclic ring selected from the group consisting of 1-indolinyl, morpholino, and piperidino, the heterocyclic substituent is C$_1$–C$_4$ alkyl or C$_1$–C$_4$ alkoxy; or W is —OR$_9$ wherein R$_9$ is C$_1$–C$_3$ alkyl. Most preferably, R$_5$ is hydroxymethyl, acetoxymethyl, morpholinocarbonyl, or piperidinocarbonyl.

In graphic formula I, each R$_6$ and R$_7$ may be selected from the group consisting of aryl, i.e., phenyl or naphthyl, mono (C$_1$–C$_6$)alkoxyaryl, di(C$_1$–C$_6$)alkoxyaryl, mono(C$_1$–C$_6$) alkylaryl, di(C$_1$–C$_6$)alkylaryl, bromoaryl, chloroaryl, fluoroaryl, C$_3$–C$_7$ cycloalkylaryl, C$_3$–C$_7$ cycloalkyl, C$_3$–C$_7$ cycloalkyloxy, C$_3$–C$_7$ cycloalkyloxy(C$_1$–C$_6$)alkyl, C$_3$–C$_7$ cycloalkyloxy(C$_1$–C$_6$)alkoxy, aryl(C$_1$–C$_6$)alkyl, aryl (C$_1$–C$_6$)alkoxy, aryloxy, aryloxy(C$_1$–C$_6$)alkyl, aryloxy (C$_1$–C$_6$)alkoxy, mono- and di(C$_1$–C$_6$)alkylaryl(C$_1$–C$_6$)alkyl, mono- and di(C$_1$–C$_6$)alkoxyaryl(C$_1$–C$_6$)alkyl, mono- and di(C$_1$–C$_6$)alkylaryl(C$_1$–C$_6$)alkoxy, mono- and di(C$_1$–C$_6$) alkoxyaryl(C$_1$–C$_6$)alkoxy, amino, mono(C$_1$–C$_6$)alkylamino, di(C$_1$–C$_6$)alkylamino, diarylamino, N—(C$_1$–C$_6$) alkylpiperazino, N-arylpiperazino, aziridino, indolino, piperidino, arylpiperidino, morpholino, thiomorpholino, tetrahydroquinolino, tetrahydroisoquinolino, pyrryl, C$_1$–C$_6$ alkyl, C$_1$–C$_6$ bromoalkyl, C$_1$–C$_6$ chloroalkyl, C$_1$–C$_6$ fluoroalkyl, C$_1$–C$_6$ alkoxy, mono(C$_1$–C$_6$)alkoxy(C$_1$–C$_4$) alkyl, acryloxy, methacryloxy, bromo, chloro and fluoro, and p and q are each the integers 0, 1 or 2. Preferably, each R$_6$ and R$_7$ is C$_1$–C$_4$ alkyl, C$_1$–C$_4$ alkoxy, chloro or fluoro, and p and q are each the integers 0, 1 or 2. More preferably, each R$_6$ and R$_7$ is C$_1$–C$_3$ alkyl or C$_1$–C$_3$ alkoxy, and p and q are each the integers 0 or 1.

Compounds represented by graphic formula I may be prepared by the following described Reactions A and B. In Reaction A, the fluoranthene compounds represented by graphic Formula II may be purchased or prepared by the methods described by Neil Campbell et al, in J. Chem. Soc., pages 1555–1559 (1949), pages 1511–1513 (1963), and pages 1697–1700 (1969), and in Chem. Abs., Vol 55 #24703i (1961); by Adolf Sieglitz et al, in Chem. Abs., Vol 58, #7882b and Vol 59, #15230h (1963); and by M. I. Shenbor et al, in J. Org. Chem. of the USSR, Vol 4, pp 2124–2127 (1968). The fluoranthene compounds represented by graphic formula II are reacted with lead acetate (Pb(OAc)$_2$) in acid, such as acetic acid, to form the 3-acetoxyfluoranthene compounds represented by graphic formula III. Reaction of compound III with a base such as sodium hydroxide yields the corresponding 3-hydroxyfluoranthenes represented by graphic formula IV. Nitrosation of compound IV with sodium nitrite in an acid such as acetic acid forms the corresponding 2-nitroso-3-hydroxyfluoranthenes represented by graphic formula V.

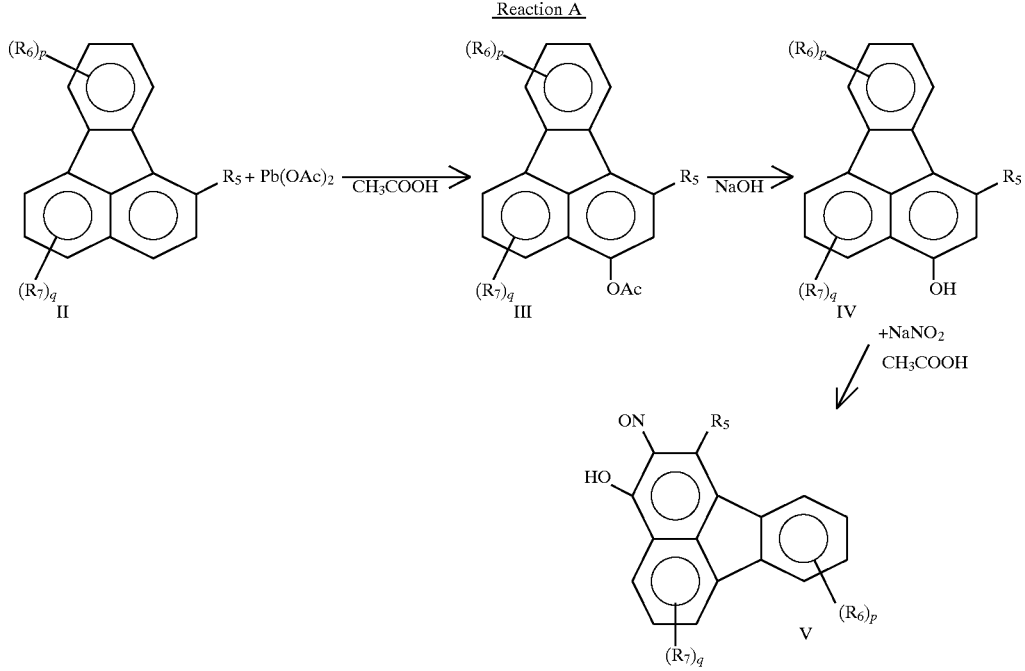

Reaction A

In Reaction B, the hydroxy nitroso compound represented by graphic formula V is coupled with a Fischer's base represented by graphic formula VI, (which may be purchased or prepared using the methods described by Brian Robinson, *The Fischer Indole Synthesis*, John Wiley and Sons, 1982) in a suitable solvent such as chloroform to form compounds represented by graphic formula I.

Reaction B

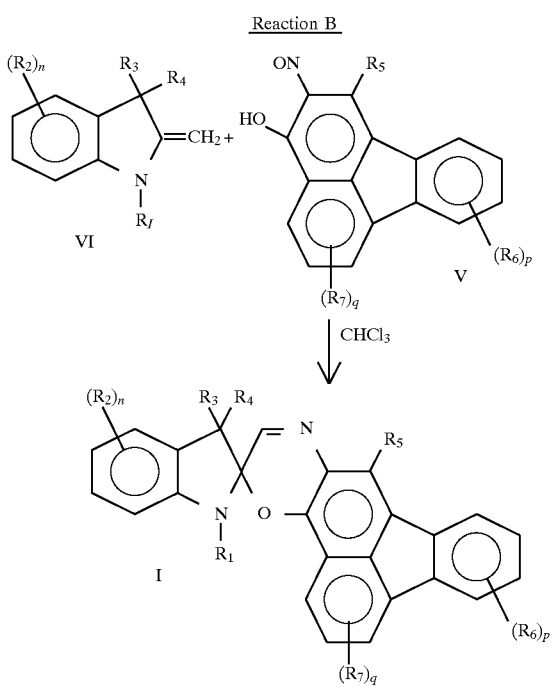

On irradiation of the compounds of graphic formula I with ultraviolet light, the fluoranthenoxazine ring is believed to open reversibly at the carbon-oxygen bond between the spiro carbon atom and the ring oxygen. The formation of the open form of the colorless compound is believed to be responsible for the coloring observed on exposure to ultraviolet light. The colored form of the photochromic compounds of graphic formula I fades to the colorless state at normal ambient temperatures when the ultraviolet light source is removed. The fluoranthenoxazines represented by graphic formula I exhibit color changes from colorless to colors ranging from green to blue.

Examples of contemplated fluoranthenoxazine compounds within the scope of the invention include the following:

(a) 1,3,3-trimethyl-spiro[indoline-2,5'-3H-fluorantheno[3,2-b][1,4]oxazine];

(b) 1,3,3,4,5 (or 1,3,3,5,6)-pentamethyl-spiro[indoline-2,5'-3H-fluorantheno[3,2-b][1,4]oxazine];

(c) 1-propyl-3,3,4,5 (or 3,3,5,6)-tetramethyl-spiro[indoline-2,5'-3H-fluorantheno[3,2-b][1,4]oxazine]; and (d) 1-methoxyethyl-3,3-dimethyl-spiro[indoline-2,5'-3H-fluorantheno[3,2-b][1,4]oxazine].

It is contemplated that the organic photochromic fluoranthenoxazines of the present invention may be used alone, in combination with other fluoranthenoxazines of the present invention, or in combination with one or more other appropriate complementary organic photochromic materials, i.e., organic photochromic compounds having at least one activated absorption maxima within the range of between about 400 and 700 nanometers, or substances containing same, which color when activated to an appropriate hue, and such photochromic compounds/materials may be associated with or incorporated, e.g., dissolved or dispersed, in a polymeric organic host material used to prepare photochromic articles.

Other than where otherwise indicated, all numbers expressing wavelengths, quantities of ingredients or reaction conditions used herein are to be understood as modified in all instances by the term "about".

Examples of complementary organic photochromic compounds include other fluoranthenoxazines, naphthopyrans, chromenes and oxazines; benzopyran compounds having substituents at the 2-position of the pyran ring including a dibenzo-fused 5 member heterocyclic compound and a substituted or unsubstituted heterocyclic ring, such as a benzothieno or benzofurano ring fused to the benzene portion of the benzopyrans, spiro(benzindoline)naphthopyrans, spiro(indoline)benzopyrans, spiro(indoline)naphthopyrans, spiro(indoline)quinopyrans, spiro(indoline)pyrans, spiro(indoline)napthoxazines, spiro(indoline)pyridobenzoxazines, spiro(benzindoline)pyridobenzoxazines, spiro(benzindoline)naphthoxazines, spiro(indoline)benzoxazines, and mixtures of such photochromic compounds. Many of such photochromic compounds are described in the open literature, e.g., U.S. Pat. Nos. 3,562,172; 3,567,605; 3,578,602; 4,215,010; 4,342,668; 4,816,584; 4,818,096; 4,826,977; 4,880,667; 4,931,219; 5,066,818; 5,238,931; 5,274,132; 5,384,077; 5,405,958; 5,429,774; 5,458,814; 5,466,398; 5,514,817; 5,552,090; 5,552,091; 5,565,146; 5,573,712; 5,578,252; 5,645,767 and Japanese Patent Publication 62/195383. Spiro(indoline) pyrans are also described in the text, *Techniques in Chemistry*, Volume III, "Photochromism", Chapter 3, Glenn H. Brown, Editor, John Wiley and Sons, Inc., New York, 1971.

Other complementary photochromic substances contemplated are photochromic metal-dithizonates, e.g. mercury dithizonates which are described in, for example, U.S. Pat. No. 3,361,706, fulgides and fulgimides, e.g. the 3-furyl and 3-thienyl fulgides and fulgimides which are described in U.S. Pat. No. 4,931,220 at column 20, line 5 through column 21, line 38.

The disclosures relating to the photochromic compounds found in the aforedescribed patents are incorporated herein, in toto, by reference. The photochromic articles of the present invention may contain one photochromic compound or a mixture of photochromic compounds, as desired.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds. Neutral gray and neutral brown colors are preferred.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): x=0.260 to 0.400, y=0.280 to 0.400 following activation to 40 percent luminous transmission by exposure to solar radiation (Air Mass 1 or 2).

The amount of photochromic substance or composition containing same applied to, associated with or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from 0.05 to 1.0, e.g., from 0.1 to 0.45, milligrams per square centimeter of surface to which the photochromic substance(s) is incorporated or applied.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating or film placed on the surface of the host material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

The host material will usually be transparent, but may be translucent or even opaque. The host material need only be transparent to that portion of the electromagnetic spectrum, which activates the photochromic substance, i.e., that wavelength of ultraviolet (UV) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

The photochromic compounds of the present invention may be present in an organic solvent or an organic polymeric host. The organic solvent may be selected from the group consisting of benzene, toluene, methyl ethyl ketone, acetone, ethanol, tetrahydrofurfuryl alcohol, N-methyl pyrrolidinone, 2-methoxyethyl ether, xylene, cyclohexane, 3-methyl cyclohexanone, ethyl acetate, tetrahydrofuran, methanol, methyl propinate, ethylene glycol and mixtures thereof. Preferably, the organic solvent is selected from the group consisting of acetone, ethanol, tetrahydrofurfuryl alcohol, 2-methoxyethyl ether, 3-methyl cyclohexanone, N-methyl pyrrolidinone and mixtures thereof.

Preferably, the organic polymeric host material is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials are polymers prepared from individual monomers or mixtures of monomers selected from the following groups:

(a) diacrylate or dimethacrylate compounds represented by graphic formula VII:

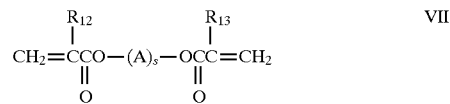

wherein $R_{12}$ and $R_{13}$ may be the same or different and are hydrogen or methyl, A is methylene, i.e., $(CH_2)$, and s is an integer of from 1 to 20;

(b) diacrylate or dimethacrylate compounds represented by graphic formula VIII:

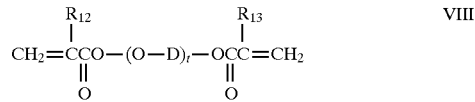

wherein D is $CH_2CR_{13}R_{14}$, $R_{14}$ being hydrogen or methylene, and t is an integer of from 1 to 50; and (c) an acrylate or a methacrylate compound having an epoxy group represented by graphic formula IX:

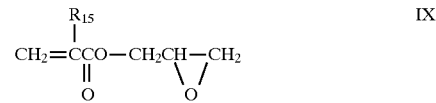

wherein $R_{15}$ is hydrogen or methyl.

In graphic formulae VII, VIII and IX, like letters used with respect to the definitions of different substituents have the same meaning.

Examples of diacrylate or dimethacrylate compounds represented by graphic formulae VII and VIII include diethylene glycol dimethacrylate, triethylene glycol dimethacrylate, etc., butanediol dimethacrylate and poly (oxyalkylene dimethacrylates), e.g., polyethylene glycol (600) dimethacrylate. Examples of acrylate or methacrylate compounds represented by graphic formula IX include glycidyl acrylate and glycidyl methacrylate.

Further examples of polymeric organic host materials which may be used with the photochromic compounds described herein include: polymers, i.e., homopolymers and copolymers, of the monomers and mixtures of monomers represented by graphic formulae VII, VIII and IX, bis(allyl carbonate) monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol polyacrylate monomers, such as ethoxylated trimethylol propane triacrylate monomers, urethane acrylate monomers, such as those described in U.S. Pat. No. 5,373,033, and vinylbenzene monomers, such as those described in U.S. Pat. No. 5,475,074 and styrene; polymers, i.e., homopolymers and copolymers, of polyfunctional, e.g., mono-, di- or multi-functional, acrylate and/or methacrylate monomers, poly($C_1$–$C_{12}$ alkyl methacrylates), such as poly(methyl methacrylate), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers, e.g., ethyl acrylate, butyl acrylate.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis (allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups, as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile.

More particularly, contemplated is use of the photochromic fluoranthenoxazines of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66. Specifically contemplated are optical resins sold by PPG Industries, Inc. under the CR-designation, e.g., CR-307 and CR-407.

The present invention is more particularly described in the following examples which are intended as illustrative only, since numerous modifications and variations therein will be apparent to those skilled in the art.

EXAMPLE 1

Step 1

Fluoranthene (20 grams) and lead acetate (25 grams) were added to a reaction flask containing glacial acetic acid (100 milliliters (mL)) and stirred overnight at 70° C. The mixture was cooled to room temperature to precipitate the lead acetate and filtered. Water (500 mL) was added to the filtrate followed by two extractions with 50 mL diethyl ether each time. The ether extracts were combined, dried and concentrated. The concentrate was crystallized from a hexane:ethane (1:1) mixture. The crystals were removed via filtration and dried, yielding 11 grams of product. The crystals also contained some starting material. A nuclear magnetic resonance (NMR) spectrum showed the predominant product to have a structure consistent with 3-acetoxyfluoranthene.

Step 2

The product of Step 1 (5 grams, 0.019 mole) was added to a reaction flask containing 10 percent sodium hydroxide solution (50 mL) and refluxed for one half hour. The reaction mixture was cooled to room temperature and acidified with a dilute hydrochloric acid solution. The resulting precipitate was filtered, washed with water and air dried, yielding 3.8 grams of product. An NMR spectrum showed the product to have a structure consistent with 3-hydroxyfluoranthene.

Step 3

The product of Step 2 was added to a reaction flask containing glacial acetic acid (25 mL) and stirred at 0° C. Sodium nitrite (0.015 mole) in water (5 mL) was added dropwise to the mixture and stirred for two hours. The resulting precipitate was filtered, washed with water and air dried, yielding 3.0 grams of product. An NMR spectrum showed the product to have a structure consistent with 2-nitroso-3-hydroxyfluoranthene.

Step 4

The nitroso compound of Step 3 (2 grams) and 1,3,3-trimethyl-2-methylene indole were added to a reaction flask containing chloroform (50 mL) and refluxed for twelve hours. The solvent was evaporated and the concentrate was passed through a silica gel column. The fractions containing the desired product were separated and combined. The solvent from the combined fractions was further evaporated yielding 1.2 grams of a product having a melting point of 186°–187° C. An NMR spectrum showed the product to have a structure consistent with 1,3,3-trimethyl-spiro[indoline-2,5'-3H-fluorantheno[3,2-b][1,4]oxazine].

EXAMPLE 2

Part A

Testing was done with the photochromic compound described in Example 1 in the following manner. A quantity of the photochromic compound calculated to yield a 1.5× $10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). The photochromic compound was dissolved into the monomer blend by stirring and gentle heating. After a clear solution was obtained, it was poured into a flat sheet mold having the interior dimensions of 2.2 mm×6 inches (15.24 cm)×6 inches (15.24 cm). The mold was sealed and placed in a horizontal air flow, programmable oven programmed to increase the temperature from 40° C. to 95° C. over a 5 hour interval, hold the temperature at 95° C. for 3 hours, lower it to 60° C. over a 2 hour period and then hold it at 60° C. for 16 hours. After the mold was opened, the polymer sheet was cut using a diamond blade saw into 2 inch (5.1 centimeters) test squares.

Part B

The photochromic test squares prepared in Part A were tested for photochromic response on an optical bench. Prior to testing on the optical bench, the photochromic test squares were exposed to 365 nanometer ultraviolet light for about 15 minutes to activate the photochromic compounds and then placed in a 76° C. oven for about 15 minutes to bleach or inactivate the photochromic compounds. The test squares were then cooled to room temperature, exposed to fluorescent room lighting for at least 2 hours and then kept covered for at least 2 hours prior to testing on an optical bench maintained at 72° F. (22.2° C.). The bench was fitted with a 150 watt Xenon arc lamp, a remote controlled shutter, a copper sulfate bath acting as a heat sink for the arc lamp, a Schott WG-320 nm cut-off filter which removes short wavelength radiation; neutral density filter(s) and a sample holder in which the square to be tested was inserted. The power output of the optical bench, i.e., the dosage of light that the sample lens would be exposed to, was calibrated with a photochromic test square used as a reference standard. This resulted in a power output ranging from 0.15 to 0.20 milliwatts per square centimeter (mW/cm$^2$). Measurement of the power output was made using a GRASEBY Optronics Model S-371 portable photometer (Serial #21536) with a UV-A detector (Serial #22411) or comparable equipment. The UV-A detector was placed into the sample holder and the light output was measured. Adjustments to the power output were made by increasing or decreasing the lamp wattage or by adding or removing neutral density filters in the light path.

A monitoring, collimated beam of light from a tungsten lamp was passed through the square at a small angle (approximately 30°) normal to the square. After passing through the square, the light from the tungsten lamp was directed to a detector through Spectral Energy Corp. GM-200 monochromator set at the previously determined visible lambda max of the photochromic compound being measured. The output signals from the detector were processed by a radiometer.

Change in optical density (ΔOD) was determined by inserting a test square in the bleached state into the sample holder, adjusting the transmittance scale to 100%, opening the shutter from the Xenon lamp to provide ultraviolet radiation to change the test square from the bleached state to an activated (i.e., darkened) state, measuring the transmittance in the activated state, and calculating the change in optical density according to the formula: $\Delta OD = \log(100/\%Ta)$, where %Ta is the percent transmittance in the activated state and the logarithm is to the base 10.

The optical properties of the photochromic compound in the test squares are reported in Table 1. The Δ OD/Min, which represents the sensitivity of the photochromic compound's response to UV light, was measured over the first five (5) seconds of UV exposure, then expressed on a per minute basis. The saturation optical density (Δ OD@Saturation) was taken under identical conditions as the Δ OD/Min, except UV exposure was continued for 15 minutes. The lambda max (Vis) is the wavelength in nanometers (nm) in the visible spectrum at which the maximum absorption of the activated (colored) form of the photochromic compound in a test square occurs. The lambda max (Vis) wavelength was determined by testing the photochromic test square polymerizate of Part A in a Varian Cary 3 UV-Visible spectrophotometer. The lambda (λ) max (UV) is the wavelength in nanometers in the ultraviolet range closest to the visible spectrum at which the absorption of the photochromic compound occurs. This absorption was also determined with the same spectrophotometer. The Bleach Rate (T ½) is the time interval in seconds for the absorbance of the activated form of the photochromic compound in the test squares to reach one half the highest absorbance at room temperature (72° F., 22.2° C.) after removal of the source of activating light.

TABLE 1

| (λ) max (VIS) | 610 nm |
| --- | --- |
| (λ) max (UV) | 366 nm |
| ΔOD/MIN Sensitivity | 0.41 |
| ΔOD@ Saturation | 0.36 |
| Bleach Rate (T ½) | 42 seconds |

The present invention has been described with reference to specific details of particular embodiments thereof. It is not intended that such details be regarded as limitations upon the scope of the invention except insofar as to the extent that they are included in the accompanying claims.

I claim:

1. A fluoranthenoxazine compound represented by the following graphic formula:

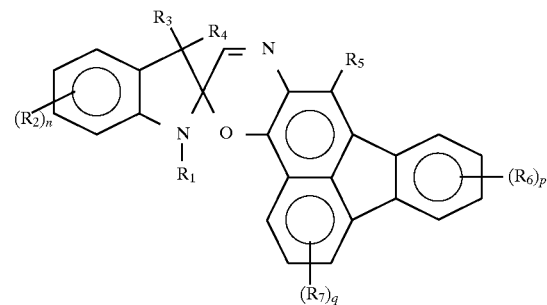

wherein,
(a) $R_1$ is selected from the group consisting of $C_1$–$C_8$ alkyl, phen($C_1$–$C_4$)alkyl, naphth($C_1$–$C_4$)alkyl, allyl, acrylyloxy($C_2$–$C_6$)alkyl, methacrylyloxy($C_2$–$C_6$)alkyl, $C_2$–$C_4$ acyloxy($C_2$–$C_6$)alkyl, carboxy($C_2$–$C_6$)alkyl, cyano($C_2$–$C_6$)alkyl, hydroxy($C_2$–$C_6$)alkyl, $C_1$–$C_6$ alkoxy($C_2$–$C_4$)alkyl and $(C_2H_4O)_m.CH_3$, wherein m is an integer from 1 to 6;
(b) $R_2$ is selected from the group consisting of $C_1$–$C_5$ alkyl, $C_1$–$C_5$ alkoxy, nitro, cyano, $C_1$–$C_8$ alkoxycarbonyl, $C_1$–$C_4$ acyloxy, halo, $C_1$–$C_4$ monohaloalkyl and $C_1$–$C_4$ polyhaloalkyl, said halo substituents being chloro, fluoro, iodo or bromo;

(c) $R_3$ and $R_4$ are each selected from the group consisting of $C_1$–$C_5$ alkyl, benzyl, phenyl, and mono- or di-substituted phenyl, said phenyl substituents being $C_1$–$C_5$ alkyl or $C_1$–$C_5$ alkoxy, or $R_3$ and $R_4$ taken together form a group selected from a cyclic ring of from 5 to 8 carbon atoms which includes the spiro carbon atom, norbornyl or adamantyl;

(d) $R_5$ is selected from the group consisting of hydrogen, —$CH_2X$ and —$C(O)W$, wherein X is halogen, hydroxy, benzoyloxy, $C_1$–$C_6$ alkoxy, $C_2$–$C_6$ acyloxy, amino, $C_1$–$C_6$ monoalkylamino, $C_1$–$C_6$ dialkylamino, morpholino, piperidino, 1-indolinyl, pyrrolidyl, trimethylsilyloxy, or the group, —$OCH(R_8)Z$, W is the group, —$OCH(R_8)Z$, or an unsubstituted, mono-substituted, or di-substituted heterocyclic ring selected from the group consisting of 1-indolinyl, morpholino, piperidino, 1-pyrrolidyl, 1-imidazolidyl, 2-imidazolin-1-yl, pyrazolidyl, pyrazolinyl and 1-piperazinyl, wherein Z is —CN, —$CF_3$, halogen, —$C(O)R_8$, or —$COOR_8$, $R_8$ is hydrogen or $C_1$–$C_6$ alkyl; said heterocyclic ring substituents being selected from $C_1$–$C_6$ alkyl and $C_1$–$C_6$ alkoxy; or W is —$OR_9$ or —$N(R_{10})R_{11}$, wherein $R_9$ is selected from the group consisting of hydrogen, allyl, $C_1$–$C_6$ alkyl, phenyl, mono($C_1$–$C_6$) alkyl substituted phenyl, mono($C_1$–$C_6$)alkoxy-substituted phenyl, phenyl($C_1$–$C_3$)alkyl, mono($C_1$–$C_6$) alkyl substituted phenyl($C_1$–$C_3$)alkyl, mono($C_1$–$C_6$) alkoxy substituted phenyl($C_1$–$C_3$)alkyl, $C_1$–$C_6$ alkoxy($C_2$–$C_4$)alkyl, and $C_1$–$C_6$ haloalkyl; and $R_{10}$ and $R_{11}$ are each selected from the group consisting of hydrogen, $C_1$–$C_6$ alkyl, $C_5$–$C_7$ cycloalkyl, phenyl and mono- or di- substituted phenyl; each of said phenyl substituents being $C_1$–$C_6$ alkyl or $C_1$–$C_6$ alkoxy and each of said halogen or halo groups in this part (d) being fluoro or chloro;

(e) each $R_6$ and $R_7$ is selected from the group consisting of aryl, mono($C_1$–$C_6$)alkoxyaryl, di($C_1$–$C_6$)alkoxyaryl, mono($C_1$–$C_6$)alkylaryl, di($C_1$–$C_6$)alkylaryl, bromoaryl, chloroaryl, fluoroaryl, $C_3$–$C_7$ cycloalkylaryl, $C_3$–$C_7$ cycloalkyl, $C_3$–$C_7$ cycloalkyloxy, $C_3$–$C_7$ cycloalkyloxy($C_1$–$C_6$)alkyl, $C_3$–$C_7$ cycloalkyloxy($C_1$–$C_6$)alkoxy, aryl($C_1$–$C_6$)alkyl, aryl($C_1$–$C_6$)alkoxy, aryloxy, aryloxy($C_1$–$C_6$)alkyl, aryloxy($C_1$–$C_6$)alkoxy, mono- and di($C_1$–$C_6$)alkylaryl ($C_1$–$C_6$)alkyl, mono- and di($C_1$–$C_6$)alkoxyaryl($C_1$–$C_6$) alkyl, mono- and di($C_1$–$C_6$)alkylaryl($C_1$–$C_6$)alkoxy, mono- and di($C_1$–$C_6$)alkoxyaryl($C_1$–$C_6$)alkoxy, amino, mono($C_1$–$C_6$)alkylamino, di($C_1$–$C_6$)alkylamino, diarylamino, N-($C_1$–$C_6$)alkylpiperazino, N-arylpiperazino, aziridino, indolino, piperidino, arylpiperidino, morpholino, thiomorpholino, tetrahydroquinolino, tetrahydroisoquinolino, pyrryl, $C_1$–$C_6$ alkyl, $C_1$–$C_6$ bromoalkyl, $C_1$–$C_6$ chloroalkyl, $C_1$–$C_6$ fluoroalkyl, $C_1$–$C_6$ alkoxy, mono($C_1$–$C_6$)alkoxy ($C_1$–$C_4$)alkyl, acryloxy, methacryloxy, bromo, chloro and fluoro; and (f) n, p and q are each the integer 0, 1, or 2.

2. The fluoranthenoxazine of claim 1 wherein:

(a) $R_1$ is allyl, $C_1$–$C_3$ alkoxy($C_2$–$C_4$)alkyl or $C_1$–$C_4$ alkyl;

(b) $R_2$ is $C_1$–$C_3$ alkoxy or $C_1$–$C_3$ alkyl;

(c) $R_3$ and $R_4$ are each $C_1$–$C_3$ alkyl or $R_3$ and $R_4$ taken together form a cyclic ring of from 5 to 7 carbon atoms which includes the spiro carbon atom;

(d) $R_5$ is selected from the group consisting of hydrogen, —$CH_2X$ and —$C(O)W$, wherein X is hydroxy, $C_1$–$C_4$ alkoxy, or $C_2$–$C_4$ acyloxy, W is the group, —$OCH(R_8)$ Z, or an unsubstituted or mono-substituted heterocyclic ring selected from the group consisting of 1-indolinyl, morpholino, piperidino, and 1-pyrrolidyl, wherein Z is —CN, —$C(O)R_8$, or —$COOR_8$, $R_8$ is hydrogen or $C_1$–$C_4$ alkyl; said heterocyclic ring substituents being selected from $C_1$–$C_4$ alkyl and $C_1$–$C_4$ alkoxy; or W is —$OR_9$ or —$N(R_{10})R_{11}$, wherein $R_9$ is selected from the group consisting of hydrogen, $C_1$–$C_4$ alkyl, phenyl, mono($C_1$–$C_4$)alkyl substituted phenyl, mono($C_1$–$C_4$) alkoxy substituted phenyl, phenyl($C_1$–$C_2$)alkyl, mono ($C_1$–$C_4$)alkyl substituted phenyl($C_1$–$C_2$)alkyl, mono ($C_1$–$C_4$)alkoxy substituted phenyl($C_1$–$C_2$)alkyl, mono ($C_1$–$C_4$)alkoxy($C_2$–$C_3$)alkyl, and $C_1$–$C_4$ haloalkyl; and $R_{10}$ and $R_{11}$, are each selected from the group consisting of hydrogen, $C_1$–$C_4$ alkyl, $C_5$–$C_7$ cycloalkyl, phenyl and mono- or di-substituted phenyl; each of said phenyl substituents being $C_1$–$C_4$ alkyl or $C_1$–$C_4$ alkoxy and each of said halo groups being fluoro or chloro;

(e) each $R_6$ and $R_7$ is selected from the group consisting of $C_1$–$C_4$ alkyl, $C_1$–$C_4$ alkoxy, chloro and fluoro; and (f) n, p and q are each the integer 0, 1 or 2.

3. The fluoranthenoxazine of claim 2 wherein, (a) $R_1$ is methyl or propyl;

(b) $R_2$ is methoxy or methyl;

(c) $R_3$ and $R_4$ are each methyl or ethyl;

(d) $R_5$ is selected from the group consisting of hydrogen, —$CH_2X$, and —$C(O)W$, wherein X is hydroxy, $C_1$–$C_4$ alkoxy, or $C_2$–$C_4$ acyloxy and W is an unsubstituted or monosubstituted heterocyclic ring selected from the group consisting of 1-indolinyl, morpholino, and piperidino, or W is —$OR_9$ wherein $R_9$ is $C_1$–$C_3$ alkyl;

(e) $R_6$ and $R_7$ are each $C_1$–$C_3$ alkyl or $C_1$–$C_3$ alkoxy; and (f) n, p and q are each the integer 0 or 1.

4. The fluoranthenoxazine of claim 3 wherein $R_5$ is hydroxymethyl, acetoxymethyl, morpholinocarbonyl, or piperidinocarbonyl.

5. A fluoranthenoxazine compound selected from the group consisting of:

(a) 1,3,3-trimethyl-spiro[indoline-2,5'-3H-fluorantheno [3,2-b][1,4]oxazine];

(b) 1,3,3,4,5 (or 1,3,3,5,6)-pentamethyl-spiro[indoline-2, 5'-3H-fluorantheno[3,2-b][1,4]oxazine];

(c) 1-propyl-3,3,4,5 (or 3,3,5,6)-tetramethyl-spiro [indoline-2,5'-3H-fluorantheno[3,2-b][1,4]oxazine]; and (d) 1-methoxyethyl-3,3-dimethyl-spiro[indoline-2,5'-3H-fluorantheno[3,2-b][1,4]oxazine].

6. A photochromic article comprising a polymeric organic host material and a photochromic amount of the fluoranthenoxazine compound of claim 1.

7. The photochromic article of claim 6 wherein the polymeric organic host material is selected from the group consisting of poly($C_1$–$C_{12}$ alkyl methacrylates), poly (oxyalkylene dimethacrylates), poly(alkoxylated phenol methacrylates), cellulose acetate, cellulose triacetate, cellulose acetate propionate, cellulose acetate butyrate, poly (vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

8. The photochromic article of claim 7 wherein the polymeric organic host material is a solid transparent polymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

9. The photochromic article of claim 8 wherein the photochromic compound is present in an amount of from 0.05 to 1.0 milligram per square centimeter of organic host material surface to which the photochromic substance(s) is incorporated or applied.

10. The photochromic article of claim 9 wherein said transparent polymer is an optical element.

11. The photochromic article of claim 10 wherein said optical element is a lens.

12. A photochromic article comprising a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of the fluoranthenoxazine compound of claim 4.

13. A photochromic article comprising a polymerizate of an optical organic resin monomer and a photochromic amount of the fluoranthenoxazine compound of claim 1.

14. The photochromic article of claim 13 wherein the refractive index of the polymerizate is from about 1.48 to about 1.75.

15. The photochromic article of claim 14 wherein the refractive index of the polymerizate is from about 1.495 to about 1.66.

16. A photochromic article comprising, in combination, a solid transparent polymeric organic host material, and a photochromic amount of each of (a) at least one fluoranthenoxazine compound of claim 1, and (b) at least one other organic photochromic compound having at least one activated absorption maxima within the range of between about 400 and 700 nanometers.

17. The photochromic article of claim 16 wherein the polymeric organic host material is selected from the group consisting of poly($C_1$–$C_{12}$ alkyl methacrylates), poly(oxyalkylene dimethacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of bis(allyl carbonate) monomers, polyfunctional acrylate monomers, polyfunctional methacrylate monomers, diethylene glycol dimethacrylate monomers, ethoxylated bisphenol A dimethacrylate monomers, diisopropenyl benzene monomers, ethylene glycol bismethacrylate monomers, poly(ethylene glycol) bismethacrylate monomers, ethoxylated phenol bismethacrylate monomers, alkoxylated polyhydric alcohol acrylate monomers, styrene monomers, urethane acrylate monomers, glycidyl acrylate monomers, glycidyl methacrylate monomers and diallylidene pentaerythritol monomers.

18. The photochromic article of claim 17 wherein the polymeric organic host material is a solid transparent homopolymer or copolymer selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

19. The photochromic article of claim 16 wherein the organic photochromic compound (b) is selected from the group consisting of naphthopyrans, chromenes, oxazines, metal-dithizonates, fulgides and fulgimides.

20. The photochromic article of claim 19 wherein the total amount of photochromic compound present is from 0.05 to 1.0 milligram per square centimeter of organic host material surface to which the photochromic substance(s) is incorporated or applied.

21. The photochromic article of claim 19 wherein said transparent polymeric organic host material is an optical element.

22. The photochromic article of claim 21 wherein said optical element is a lens.

23. A photochromic article comprising, in combination, a polymeric organic host material selected from the group consisting of poly(methyl methacrylate), poly(ethylene glycol bismethacrylate), poly(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers, and a photochromic amount of each of (a) at least one fluoranthenoxazine compound of claim 4, and (b) at least one other organic photochromic compound having at least one activated absorption maxima within the range of between about 400 and 700 nanometers.

* * * * *

UNITED STATES PATENT AND TRADEMARK OFFICE
CERTIFICATE OF CORRECTION

PATENT NO. : 5,808,063
DATED : 9/15/98
INVENTOR(S) : Kumar

It is certified that error appears in the above-identified patent and that said Letters Patent is hereby corrected as shown below:

Column 12, line 63, after "(b)" insert --each--.

Column 13, line 61, after "(b)" insert --each--.

Column 14, line 25, after "(b)" insert --each--.

Signed and Sealed this

Twenty-third Day of February, 1999

Attest:

Q. TODD DICKINSON

Attesting Officer

Acting Commissioner of Patents and Trademarks